(12) United States Patent
Hirasawa et al.

(10) Patent No.: US 12,734,314 B2
(45) Date of Patent: Sep. 15, 2026

(54) NEBULIZER KIT AND NEBULIZER

(71) Applicant: OMRON HEALTHCARE CO., LTD., Muko (JP)

(72) Inventors: Asa Hirasawa, Kyoto (JP); Kengo Nishiyama, Kyoto (JP); Gen Suzuki, Kanagawa (JP); Simone Abate, Brescia (IT); Davide Fraccaroli, Brescia (IT)

(73) Assignee: OMRON HEALTHCARE CO., LTD., Kyoto (JP)

(*) Notice: Subject to any disclaimer, the term of this patent is extended or adjusted under 35 U.S.C. 154(b) by 613 days.

(21) Appl. No.: 18/210,670

(22) Filed: Jun. 16, 2023

(65) Prior Publication Data

US 2023/0381431 A1 Nov. 30, 2023

Related U.S. Application Data

(63) Continuation of application No. PCT/JP2021/044538, filed on Dec. 3, 2021.

(30) Foreign Application Priority Data

Dec. 21, 2020 (JP) ................................ 2020-211592

(51) Int. Cl.
*A61M 15/00* (2006.01)
*A61M 11/02* (2006.01)
*A61M 11/06* (2006.01)

(52) U.S. Cl.
CPC ........ *A61M 15/0015* (2014.02); *A61M 11/02* (2013.01); *A61M 11/06* (2013.01);
(Continued)

(58) Field of Classification Search
CPC ................ A61M 11/00–08; A61M 15/00–085
See application file for complete search history.

(56) References Cited

U.S. PATENT DOCUMENTS 5,584,285 A * 12/1996 Salter ..................... A61M 11/06 128/203.23
5,875,774 A * 3/1999 Clementi ............. B05B 7/0012 239/338
(Continued)

FOREIGN PATENT DOCUMENTS

CN 210583295 U 5/2020
EP 0281650 A1 * 9/1988 ........... A61M 15/00
(Continued)

OTHER PUBLICATIONS

Official Communication issued in corresponding Chinese Patent Application No. 202180084667.2, mailed on Jun. 21, 2025, 7 pages.
(Continued)

*Primary Examiner* — Tu A Vo
(74) *Attorney, Agent, or Firm* — Keating & Bennett, LLP

(57) ABSTRACT

A nebulizer kit includes: a housing body that houses an atomization portion configured to atomize a liquid and includes a first opening portion and a second opening portion; and a mouthpiece in which a first attachment portion including a first check valve and configured to be attachable to and detachable from the first opening portion and a tubular second attachment portion including a second check valve and configured to be attachable to and detachable from the second opening portion are integrally configured. An inhalation attachment different from the mouthpiece is attachable to the second opening portion in a state in which the mouthpiece is removed from the housing body.

10 Claims, 9 Drawing Sheets

(52) U.S. Cl.
CPC .... *A61M 15/0018* (2014.02); *A61M 15/0021* (2014.02); *A61M 2209/06* (2013.01)

(56) References Cited

U.S. PATENT DOCUMENTS

| | | | | |
|---|---|---|---|---|
| 6,026,807 | A * | 2/2000 | Puderbaugh | A61M 15/0016 128/200.14 |
| 6,039,042 | A * | 3/2000 | Sladek | A61M 15/0016 128/205.24 |
| 6,176,234 | B1 * | 1/2001 | Salter | A61M 15/0023 128/207.14 |
| 6,732,731 | B1 * | 5/2004 | Tseng | A61M 15/0023 128/200.22 |
| 6,962,151 | B1 * | 11/2005 | Knoch | A61M 15/0015 239/338 |
| 6,994,083 | B2 * | 2/2006 | Foley | A61M 11/002 239/338 |
| 7,204,245 | B2 * | 4/2007 | Johnson | A61M 15/0086 128/205.24 |
| 10,258,758 | B1 * | 4/2019 | Faram | A61M 16/0833 |
| 10,709,852 | B2 * | 7/2020 | Engelbreth | A61M 16/0816 |
| 11,779,714 | B1 * | 10/2023 | Shargian | A61M 11/06 128/200.23 |
| 2002/0056448 | A1 * | 5/2002 | Stapleton | A61M 15/0018 128/200.14 |
| 2002/0121275 | A1 * | 9/2002 | Johnson | A61M 15/0015 128/200.22 |
| 2002/0157664 | A1 * | 10/2002 | Fugelsang | A61M 15/0021 128/200.22 |
| 2003/0062038 | A1 * | 4/2003 | Tanaka | A61M 15/00 128/200.14 |
| 2006/0137682 | A1 * | 6/2006 | Tseng | A61M 15/0025 128/200.14 |
| 2008/0083409 | A1 * | 4/2008 | Hamaguchi | A61M 16/20 128/205.24 |
| 2009/0139888 | A1 * | 6/2009 | Berry | B65D 77/0413 229/5.81 |
| 2009/0314287 | A1 * | 12/2009 | Spallek | A61M 11/06 128/200.14 |
| 2012/0227735 | A1 * | 9/2012 | Abate | A61M 15/0015 128/200.14 |
| 2013/0239956 | A1 * | 9/2013 | Schulz | A61M 15/0085 128/200.14 |
| 2014/0230811 | A1 * | 8/2014 | Von Hollen | A61M 11/06 128/200.14 |
| 2014/0263743 | A1 | 9/2014 | Esaki et al. | |
| 2016/0375206 | A1 * | 12/2016 | Gramann | A61M 15/0021 128/203.12 |
| 2017/0049976 | A1 * | 2/2017 | Reed | A61M 15/009 |
| 2017/0340846 | A1 * | 11/2017 | Gramann | A61M 11/06 |
| 2018/0008789 | A1 * | 1/2018 | Alizoti | A61M 15/0093 |
| 2019/0076605 | A1 * | 3/2019 | Tsai | A61M 15/0021 |
| 2019/0192790 | A1 | 6/2019 | Toddywala et al. | |
| 2020/0288786 | A1 * | 9/2020 | Niebling | A61K 9/0073 |
| 2021/0106772 | A1 * | 4/2021 | Hebrank | A61M 11/005 |

FOREIGN PATENT DOCUMENTS

| | | | | |
|---|---|---|---|---|
| EP | 0626180 | A1 * | 11/1994 | A61M 15/0015 |
| GB | 2358356 | A * | 7/2001 | A61M 15/0086 |
| JP | 2003-102837 | A | 4/2003 | |
| JP | 2006-255308 | A | 9/2006 | |
| JP | 2013-132473 | A | 7/2013 | |
| JP | 2019-529012 | A | 10/2019 | |

OTHER PUBLICATIONS

English translation of Official Communication issued in International Patent Application No. PCT/JP2021/044538, mailed on Jan. 11, 2022.

Official Communication issued in International Patent Application No. PCT/JP2021/044538, mailed on Jan. 11, 2022.

* cited by examiner

NEBULIZER KIT AND NEBULIZER

CROSS-REFERENCE TO RELATED APPLICATIONS

This application is a continuation of PCT application No. PCT/JP2021/044538, which was filed on Dec. 3, 2021 based on Japanese Patent Application No. 2020-211592 filed on Dec. 21, 2020, the contents of which are incorporated herein by way of reference.

BACKGROUND

The present invention relates to a nebulizer kit and a nebulizer.

A general nebulizer includes a nebulizer kit capable of generating aerosol. For example, JP2013-132473A is known as a document disclosing a nebulizer using a nebulizer kit. In addition, a nebulizer is known which is configured to inhale a drug solution by attaching different attachments (mouthpieces and inhalation masks), respectively (for example, a compressor type nebulizer NE-C28 manufactured by Omron Healthcare Co., Ltd.).

It is assumed that the inhalation mask is used by a child or an elderly person having a weak suction force. On the other hand, it is assumed that a mouthpiece is used by people having a strong suction force. A suction force is required when using the mouthpiece, and it is desired that the drug solution can be inhaled more efficiently. On the other hand, when the inhalation mask is used, it is desired that a user having a weak suction force can easily inhale the drug solution.

An object of the present invention is to provide a nebulizer kit and a nebulizer that enable a user having a weak suction force to easily inhale a drug solution and enable a user having a strong suction force to efficiently inhale the drug solution.

SUMMARY

According to one aspect of the present invention, there is provided a nebulizer kit including:

- a housing body that houses an atomization portion configured to atomize a liquid and includes a first opening portion and a second opening portion; and
- a mouthpiece in which a first attachment portion including a first check valve and configured to be attachable to and detachable from the first opening portion and a tubular second attachment portion including a second check valve and configured to be attachable to and detachable from the second opening portion are integrally configured,
- in which an inhalation attachment different from the mouthpiece is attachable to the second opening portion in a state in which the mouthpiece is removed from the housing body.

In a state in which the mouthpiece is attached to the housing body, the first check valve may take outside air into the housing body in accordance with an inhalation operation using the mouthpiece, and the second check valve may deliver exhaled air to outside of the second attachment portion in accordance with an exhalation operation using the mouthpiece.

The first opening portion and the first attachment portion may be provided with a positioning mechanism for positioning the first attachment portion with respect to the first opening portion.

The mouthpiece may include a connecting portion that connects the first attachment portion and the second attachment portion, and the connecting portion may be elastically deformable The mouthpiece may be configured such that the inhalation attachment is not attachable to the second attachment portion.

An outer diameter of at least a part of a suction port end portion of the mouthpiece may be larger than an inner diameter of an attachment portion of the inhalation attachment to the housing body.

The first opening portion may be open in a longitudinal direction of the housing body, and the second opening portion may be open in a transverse direction of the housing body.

The first opening portion may be larger than the second opening portion.

The fulcrum of a movable portion of the second check valve may be provided eccentrically to a suction port end portion side of the mouthpiece.

According to another aspect of the present application, there is provided a nebulizer including:

the nebulizer kit;

a main body portion configured to control the atomization portion; and the inhalation attachment.

DESCRIPTION OF EMBODIMENTS

Overview of Nebulizer Kit of Embodiment

First, an outline of an embodiment of a nebulizer kit according to the present invention will be described.

A nebulizer kit according to the embodiment is configured such that a first check valve that takes into outside air into a housing body of an atomization portion during an inhalation operation and a second check valve that delivers breath to the outside during an exhalation operation are integrated with a mouthpiece, and the mouthpiece is attachable to and detachable from the housing body. In a state in which the mouthpiece is removed from the housing body, an inhalation attachment different from the mouthpiece is attachable to the housing body.

With such a configuration, when another inhalation attachment is used, one of the two opening portions of the housing body to which the mouthpiece is to be attached is always in a state of being largely opened, so that the outside air can easily flow into the housing body during the inhalation operation. As a result, when the other inhalation attachment is used, a user having a weak suction force may easily inhale the drug solution. In addition, when a user having a strong suction force uses the mouthpiece, the first check valve is attached to the one opening portion of the housing body. Accordingly, a state in which the drug solution may be efficiently inhaled is always realized.

Embodiment

Hereinafter, a specific configuration example of a nebulizer kit according to the embodiment will be described.

Figure 1:
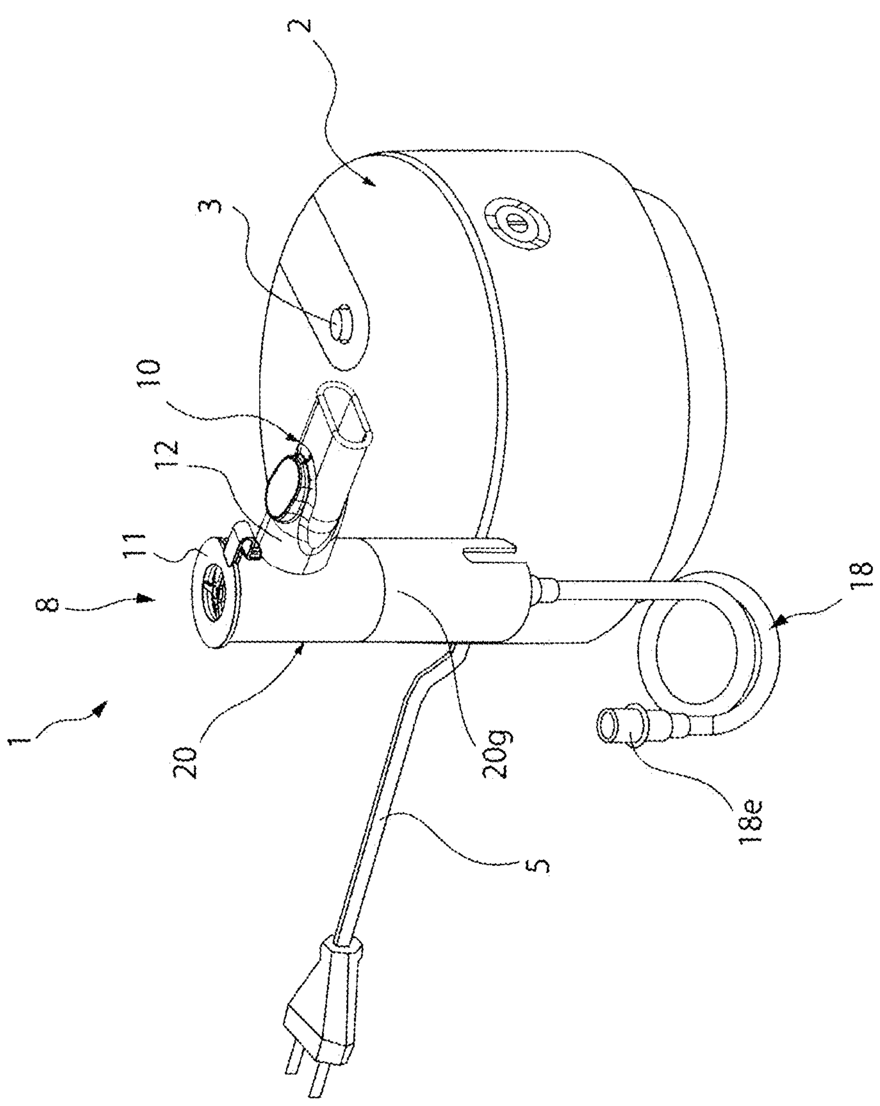
FIG. 1 is a perspective view showing a nebulizer including a nebulizer kit according to an embodiment of the present invention.

FIG. 1 is a perspective view showing a nebulizer including the nebulizer kit according to an embodiment of the present invention.

(Nebulizer Kit)

A nebulizer 1 shown in FIG. 1 includes a main body portion 2, a nebulizer kit 8 attachable to the main body portion 2, and an inhalation attachment 30 described later.

The nebulizer kit 8 includes a housing body 20 to which air is supplied from the main body portion 2, a mouthpiece 10, and a tube 18 that connects the housing body 20 and the main body portion 2. The housing body 20 is connected to the main body portion 2 by attaching a connection end 18*e* at one end portion of the tube 18 to a connection portion 3 of the main body portion 2. One configuration of the nebulizer 1 is thus configured. For example, as shown in the drawing, one end of a body portion 20*g* of the housing body 20 may be attachably and detachably held on a side surface of the main body portion 2.

(Main Body Portion)

The main body portion 2 includes a power cord 5 and the like, and includes a drive source (not shown) which is driven by external electric power supplied thereto. The main body portion 2 may supply compressed air from one end side (lower side in FIG. 1) of the housing body 20 through the tube 18 connected to the connection portion 3. In addition, the main body portion 2 may control the compressed air to be supplied, and may control an atomization amount of a liquid in an atomization portion 25 in the housing body 20 which is described later.

(Housing Body)

Figure 2:
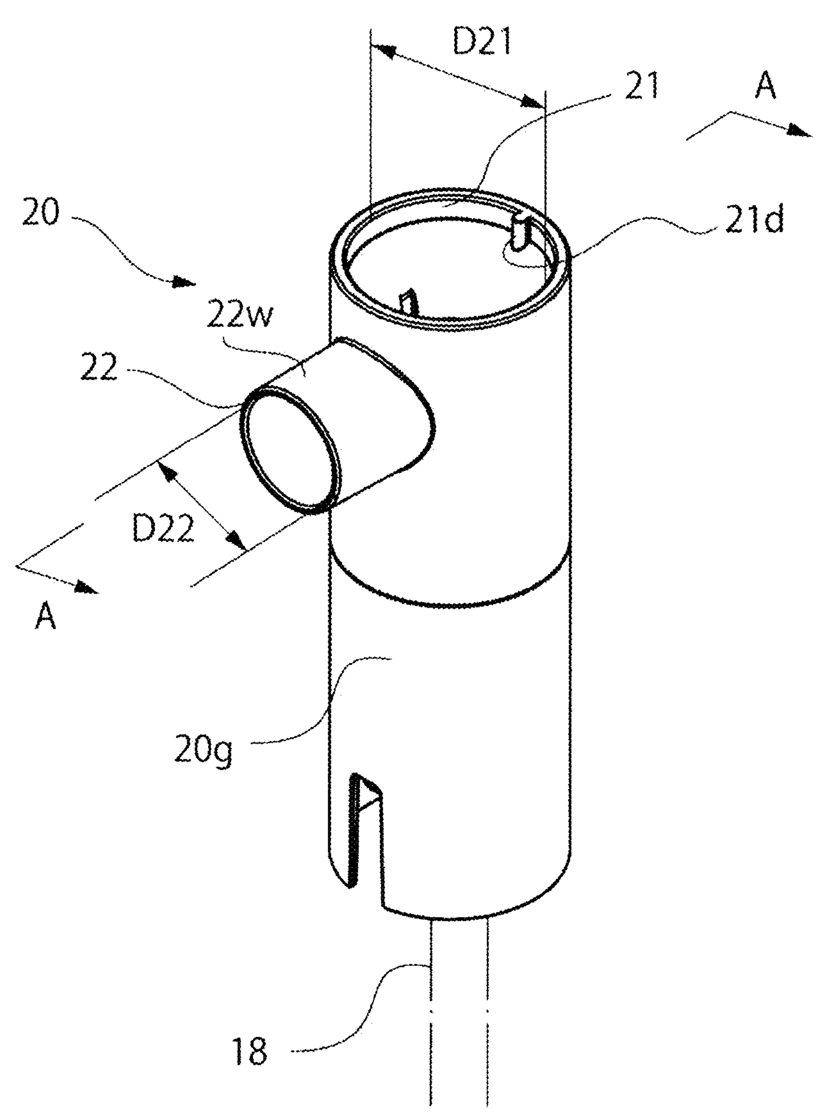
FIG. 2 is an enlarged perspective view of a housing body of the nebulizer kit.

FIG. 2 is an enlarged perspective view of the housing body 20 shown in FIG. 1.

As shown in FIG. 2, at the housing body 20, the tube 18 is connected to one end side (lower side in FIG. 2) in a longitudinal direction of the cylindrical body portion 20*g*, and a first opening portion 21 constituting a circular opening is provided on the other end side thereof (upper side in FIG. 2). In addition, a cylindrical side surface protruding wall portion 22*w* communicating with the inside of the body portion 20*g* is formed to protrude from a side surface (end surface in a transverse direction) of the body portion 20*g*, and an inner peripheral portion of the side surface protruding wall portion 22*w* constitutes a second opening portion 22. An inner diameter D21 of the first opening portion 21 is larger than an inner diameter D22 of the second opening portion 22.

(Atomization Portion)

Figure 3:
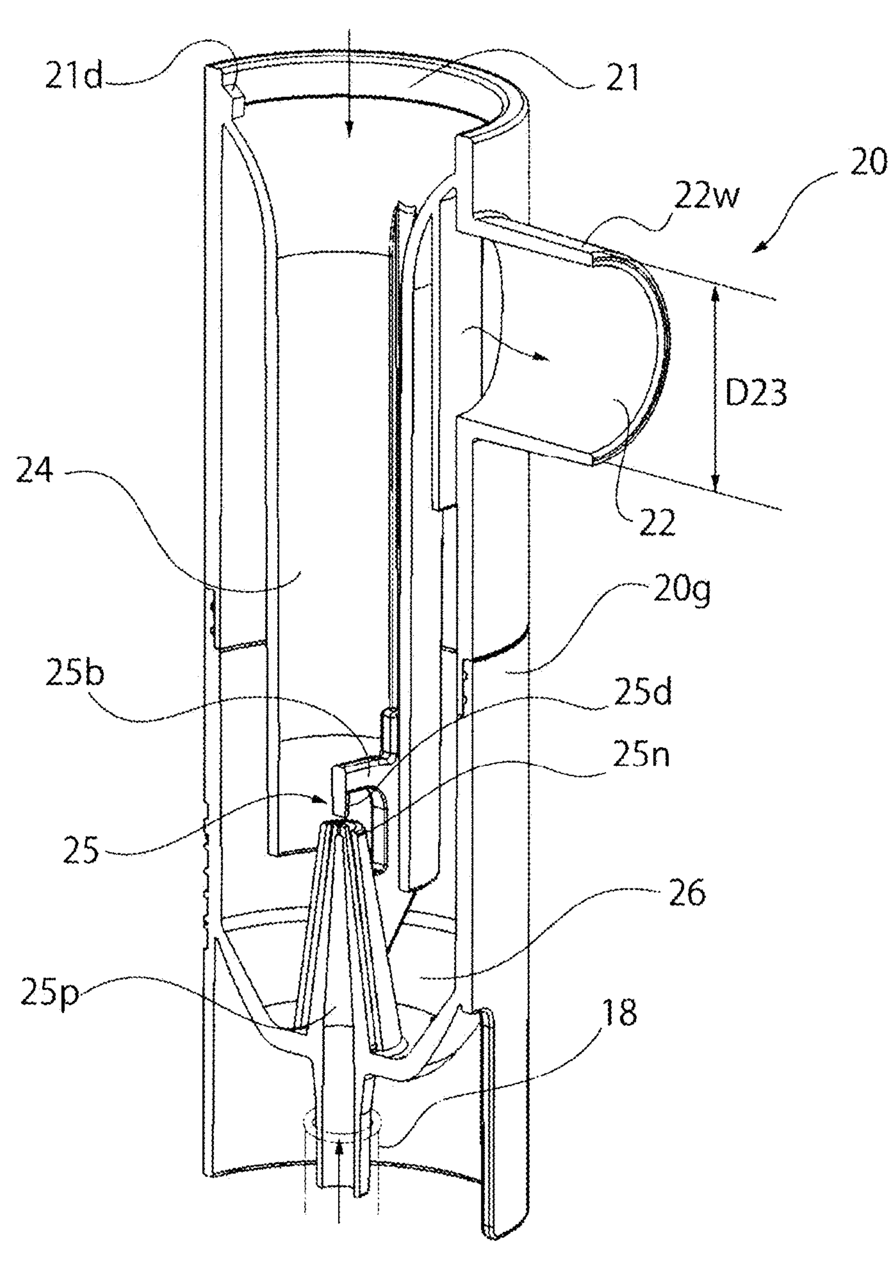
FIG. 3 is a cross-sectional view of a portion taken along a line A-A of FIG. 2.

FIG. 3 is a cross-sectional view of a portion taken along a line A-A of FIG. 2.

As shown in FIG. 3, the atomization portion 25 that atomizes the liquid is provided inside the body portion 20*g*. The atomization portion 25 includes a nozzle 25*n* provided at a tip end of a compressed air introduction pipe 25*p*, and a baffle portion 25*b* including a protrusion 25*d* protruding toward the nozzle 25*n*. The tube 18 is connected to the compressed air introduction pipe 25*p*. Inside the body portion 20*g*, a liquid storage portion 26 that stores a liquid such as a drug solution is provided around the compressed air introduction pipe 25*p*. A tubular outside air introduction pipe 24 extending from the first opening portion 21 toward the compressed air introduction pipe 25*p* and the liquid storage portion 26 is provided inside the body portion 20*g*. The atomization portion 25 is disposed at an end portion of the outside air introduction pipe 24 on a side opposite to the first opening portion 21 side. The side surface protruding wall portion 22*w* described above is formed on a side wall of the body portion 20*g* surrounding the outside air introduction pipe 24.

The compressed air introduced from the main body portion 2 into the compressed air introduction pipe 25*p* through the tube 18 is jetted through the nozzle 25*n* at the tip end of the compressed air introduction pipe 25*p*. The compressed air is jetted from the nozzle 25*n* toward the protrusion 25*d*, then collides with the protrusion 25*d* and the baffle portion 25*b*, and radially spreads in a direction changed from a direction in which the compressed air is discharged from the nozzle 25*n*. Accordingly, a negative pressure, which is lower than a surrounding pressure, is generated in the atomization portion 25 and a vicinity thereof.

Due to the action of the negative pressure in the atomization portion 25 and the vicinity thereof, the liquid (not shown) stored in the liquid storage portion 26 is sucked up to the vicinity of the atomization portion 25 from a slit-shaped introduction path provided in the compressed air introduction pipe 25*p*. The sucked liquid collides with the protrusion 25*d* and the baffle portion 25*b* together with the compressed air, is smashed, and is atomized into atomized particles (fine liquid droplets).

The atomized particles are added to the outside air introduced from the first opening portion 21 through the outside air introduction pipe 24, thereby generating aerosol in the atomization portion 25. The aerosol moves toward the second opening portion 22 through the outside of the outside air introduction pipe 24 in a swirling manner.

(Mouthpiece)

Figure 4:
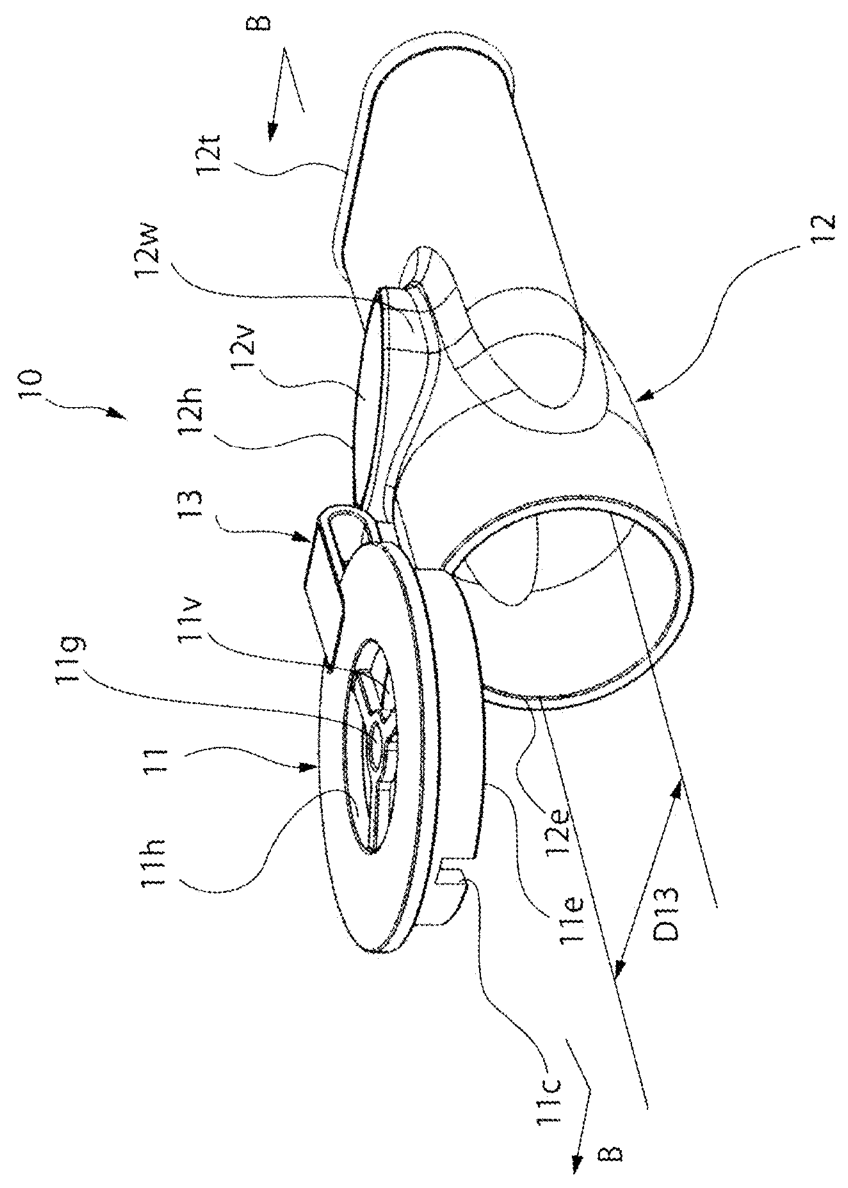
FIG. 4 is an enlarged perspective view of a mouthpiece as viewed from an attachment end portion side.
Figure 5:
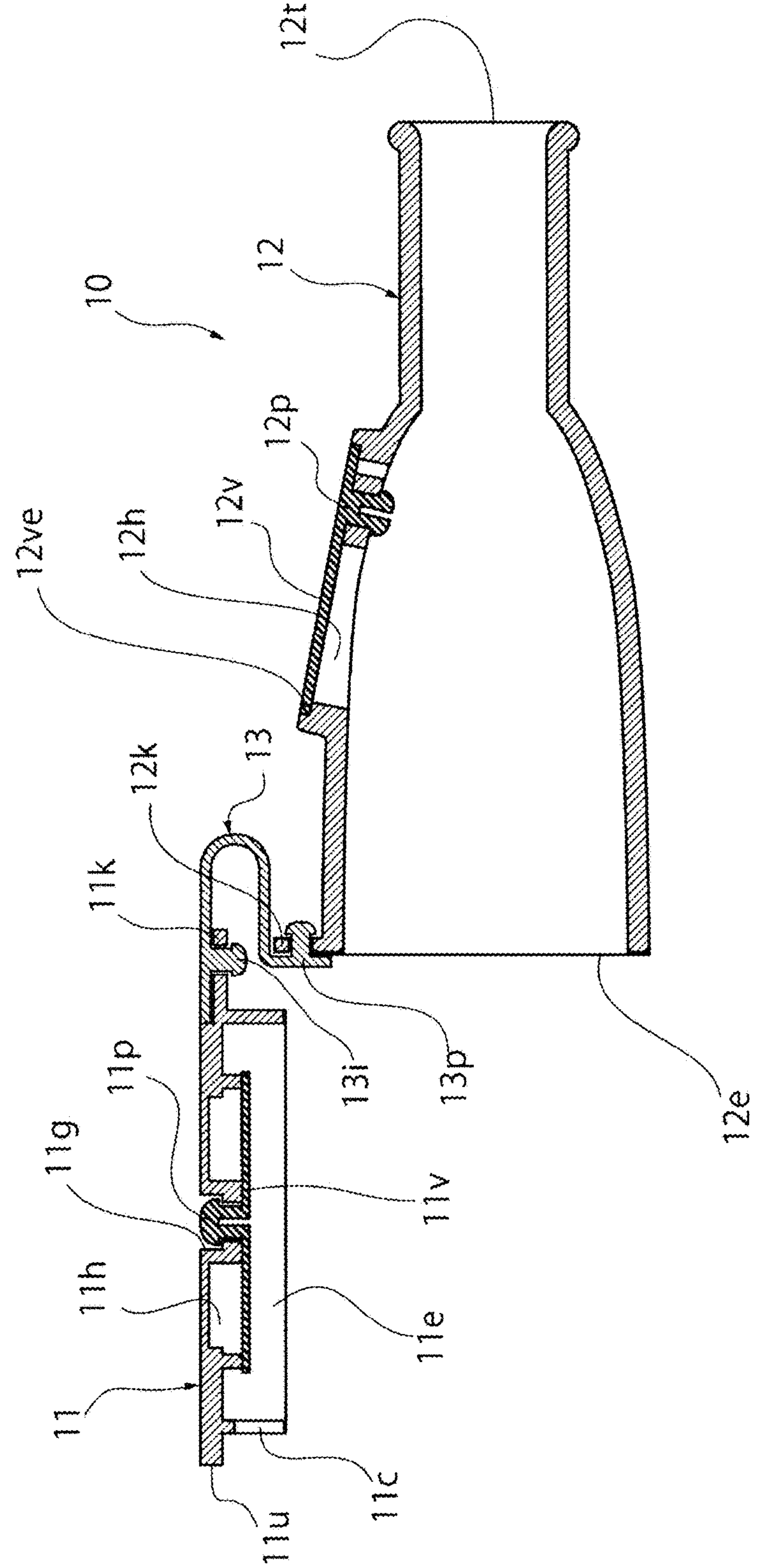
FIG. 5 is a cross-sectional view of a portion taken along a line B-B in FIG. 4.

FIG. 4 is an enlarged perspective view of the mouthpiece 10 shown in FIG. 1 as viewed from the housing body 20 side. FIG. 5 is a cross-sectional view of a portion taken along a line B-B in FIG. 4.

As shown in FIGS. 4 and 5, the mouthpiece 10 includes a substantially disk-shaped first attachment portion 11, a tubular second attachment portion 12, and a connecting portion 13 that connects the first attachment portion 11 and the second attachment portion 12 to each other, and these three members are integrally configured. Specifically, the first attachment portion 11 and the connecting portion 13 are fixed to each other, and the second attachment portion 12 and the connecting portion 13 are fixed to each other, whereby these three members are integrated. The term "fixed" refers to a state in which these members are firmly connected by adhesion, screwing, press-fitting, or the like so as not to be easily separated.

The first attachment portion 11 is provided with an inhalation opening 11*h* penetrating therethrough in a thickness direction thereof. The first attachment portion 11 includes an outer surface portion flu having a large diameter and an attachment fitting portion 11*e* having a smaller diameter than the outer surface portion 11*u*. The attachment fitting portion 11*e* has a diameter adjusted to the inner diameter D21 (see FIG. 2) of the first opening portion 21 so as to be fitted into the inside of the first opening portion 21.

The first opening portion 21 and the first attachment portion 11 are provided with a positioning mechanism capable of positioning the first attachment portion 11 with respect to the first opening portion 21. The positioning mechanism includes cutout recesses 11*c* (see FIG. 4) provided in the attachment fitting portion 11*e* from a lower end side to an outer side surface, and positioning protrusions 21*d* (see FIG. 2) provided in an inner peripheral wall portion of the first opening portion 21 so as to be fitted into the cutout recesses 11*c*.

The inhalation opening 11*h* of the first attachment portion 11 is provided with a first check valve 11*v* in a manner to close the inhalation opening 11*h*. The first check valve 11*v* is a flat plate-shaped sheet member, and is provided with an attachment protrusion 11*p* at the center thereof. The attachment protrusion 11*p* is fitted into a valve attachment portion 11*g* provided at a center of the inhalation opening 11*h*.

One end side (the first attachment portion 11 side) of a body portion of the second attachment portion 12 is configured as a cylindrical attachment end portion 12*e*. The attachment end portion 12*e* is configured to be fitted to the side surface protruding wall portion 22*w* of the housing body 20. In other words, an inner diameter D13 of the attachment end portion 12*e* is formed to be slightly larger than an outer diameter D23 of the side surface protruding wall portion 22*w* so as to be fitted to the side surface protruding wall portion 22*w*. In addition, the other end side (a side opposite to the first attachment portion 11 side) of the body portion of the second attachment portion 12 is configured as a suction port end portion 12*t* having a flat cylindrical portion. On a side surface (middle upper side in FIGS. 4 and 5) of the body portion of the second attachment portion 12, an exhalation opening 12*h* is provided by a protruding wall portion 12*w* slightly protruding from the side surface thereof. A second check valve 12*v* is attached to the exhalation opening 12*h* from the outside in a manner to close the exhalation opening 12*h*.

The second check valve 12*v* is a flat plate-shaped sheet member similarly to the first check valve 11*v*, and is formed in, for example, an elliptical shape having a long axis along a longitudinal direction (axial direction, left-right direction in FIG. 5) of the second attachment portion 12. An attachment portion 12*p* of the second check valve 12*v* is provided at a position closer to the suction port end portion 12*t* than a center of the exhalation opening 12*h*. That is, the second check valve 12*v* is configured such that a fulcrum (the attachment portion 12*p*) of a movable portion when the second check valve 12*v* moves as a valve is eccentrically provided on the suction port end portion 12*t* side with respect to the exhalation opening 12*h*, and a free end portion 12*ve*, which is an end portion on a side opposite to the suction port end portion 12*t* side opens and closes.

(Connecting Portion)

As shown in FIG. 5, the connecting portion 13 is formed, for example, in a strip shape and in a relatively thin elongated shape, and insertion pin portions 13*i* and 13*p* whose distal ends are tapered are provided at both end portions thereof. The first attachment portion 11 is provided with an attachment piece 11*k* having a hole into which the insertion pin portion 13*i* is inserted and engaged. The second attachment portion 12 is provided with an attachment piece 12*k* having a hole into which the insertion pin portion 13*p* is inserted and engaged. The connecting portion 13 is preferably made of rubber or resin that is relatively flexible and elastically deformable.

Hereinafter, a use state of the mouthpiece 10 will be described.

Figure 6:
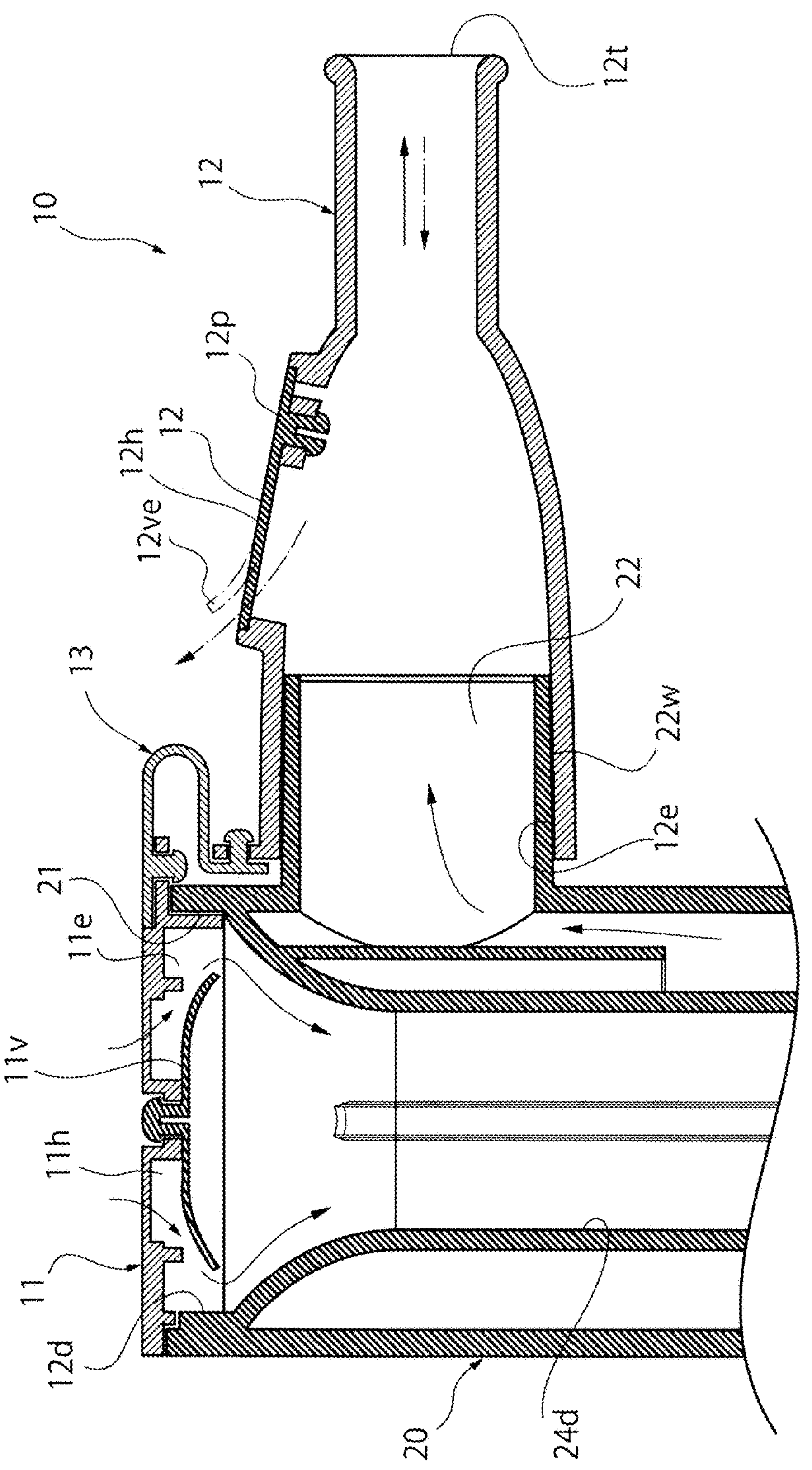
FIG. 6 is an enlarged cross-sectional view of a state in which the mouthpiece shown in FIG. 4 is attached to a housing body.

FIG. 6 is an enlarged cross-sectional view of a state in which the mouthpiece 10 shown in FIG. 4 is attached to the housing body 20.

As shown in FIG. 6, the mouthpiece 10 is attached to the housing body 20 by fitting the first attachment portion 11 into the first opening portion 21 and fitting the attachment end portion 12*e* of the second attachment portion 12 into the side surface protruding wall portion 22*w* of the second opening portion 22. In this state, the user holds the body portion 20*g* of the housing body 20 with his/her hand, and performs the inhalation operation and the exhalation operation in a state in which the user holds the suction port end portion 12*t* in his/her mouth.

During the inhalation operation, as shown in FIG. 6, the first check valve 11*v* is deformed to the inside of the housing body 20 due to the negative pressure, and the inhalation opening 11*h* of the first attachment portion 11 is connected to the outside air introduction pipe 24. Accordingly, the outside air is taken into the housing body 20 from the inhalation opening 11*h*. At this time, the second check valve 12*v* closes the exhalation opening 12*h* due to the negative pressure. The outside air taken into the housing body 20 passes through the outside air introduction pipe 24 and is added to the drug solution atomized into the atomized particles in the atomization portion 25, thereby generating the aerosol. As indicated by solid arrows in FIG. 6, the generated aerosol passes through the outside of the outside air introduction pipe 24 to reach the second opening portion 22, and is sucked into a human body from the second opening portion 22 through the second attachment portion 12 of the mouthpiece 10.

During the exhalation operation, the inside of the mouthpiece 10 and the housing body 20 is pressurized. At this time, the first check valve 11*v* closes the inhalation opening 11*h* by being pressurized. On the other hand, the second check valve 12*v* is deformed by pressurization so that the free end portion 12*ve* is warped outward, and the exhaled air is discharged to the outside of the mouthpiece 10 as indicated by a long dashed short dashed line arrow in FIG. 6.

Figure 7:
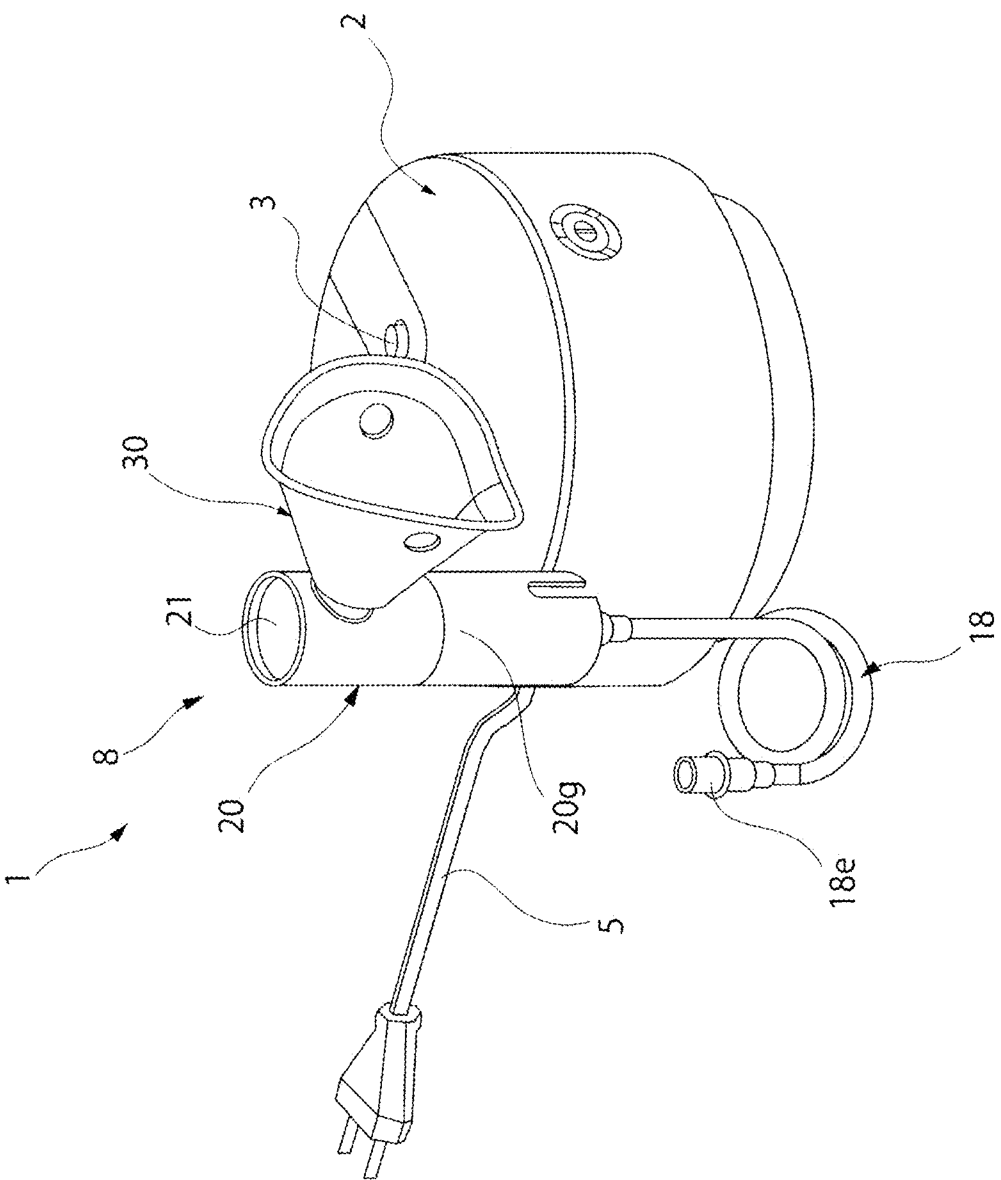
FIG. 7 is a perspective view showing a state in which an inhalation attachment is attached to the housing body of the nebulizer kit shown in FIG. 1.

FIG. 7 is a perspective view showing a state in which the inhalation attachment is attached to the housing body 20 of the nebulizer kit 8 shown in FIG. 1.

In the nebulizer 1 shown in FIG. 7, the inhalation attachment 30 is attached to the housing body 20 instead of the mouthpiece 10. In this way, the nebulizer kit 8 is configured such that the inhalation attachment 30 different from the mouthpiece 10 is attachable to the side surface protruding wall portion 22*w* (second opening portion 22) in a state in which the mouthpiece 10 is removed from the housing body 20.

(Inhalation Attachment)

Figure 8:
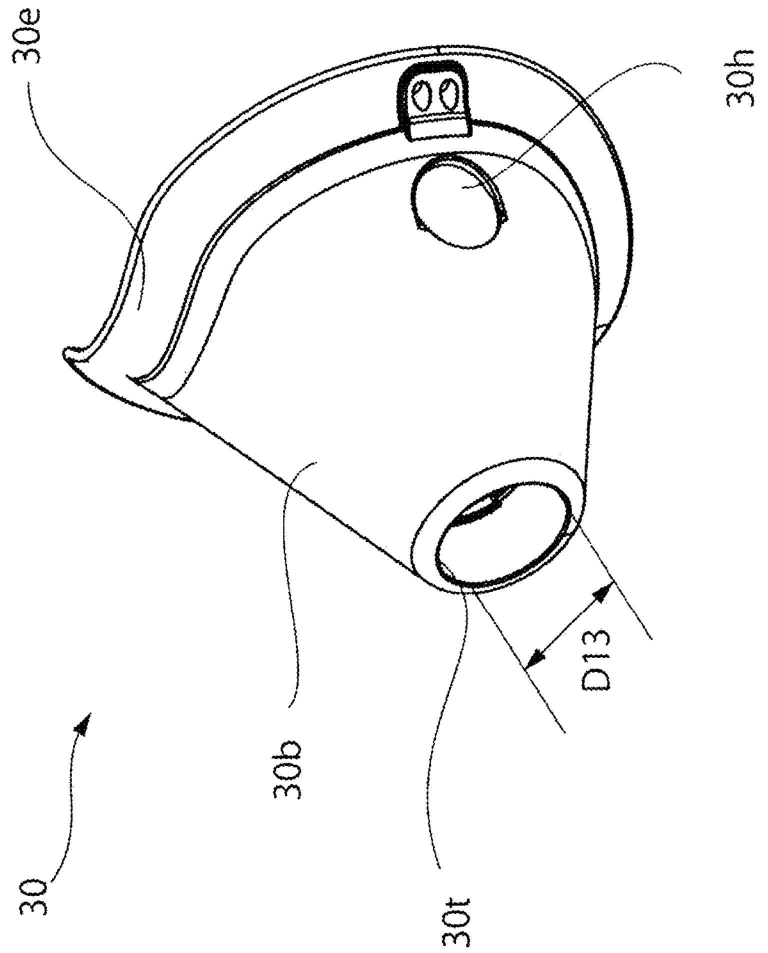
FIG. 8 is an enlarged perspective view of the inhalation attachment shown in FIG. 7.

FIG. 8 is an enlarged perspective view of the inhalation attachment 30.

As shown in FIG. 8, in the inhalation attachment 30, an attachment hole 30*t* is provided on a tip end side (left side in FIG. 8) of a funnel body portion 30*b* having a substantially funnel shape. The attachment hole 30*t* has the same inner diameter (inner diameter D13) as the attachment end portion 12*e* of the mouthpiece 10, and is configured to be fitted to the side surface protruding wall portion 22*w*. Therefore, as shown in FIG. 7, in a state in which the mouthpiece 10 is removed from the housing body 20, the inhalation attachment 30 may be attached to the side surface protruding wall portion 22$w$ of the housing body 20. The inhalation attachment 30 further includes, on a side opposite to the attachment hole 30$t$, a corresponding edge portion 30$e$ having a shape that fits the face to cover a region including the mouth and the nose. Two side openings are formed in the funnel body portion 30$b$.

Figure 9:
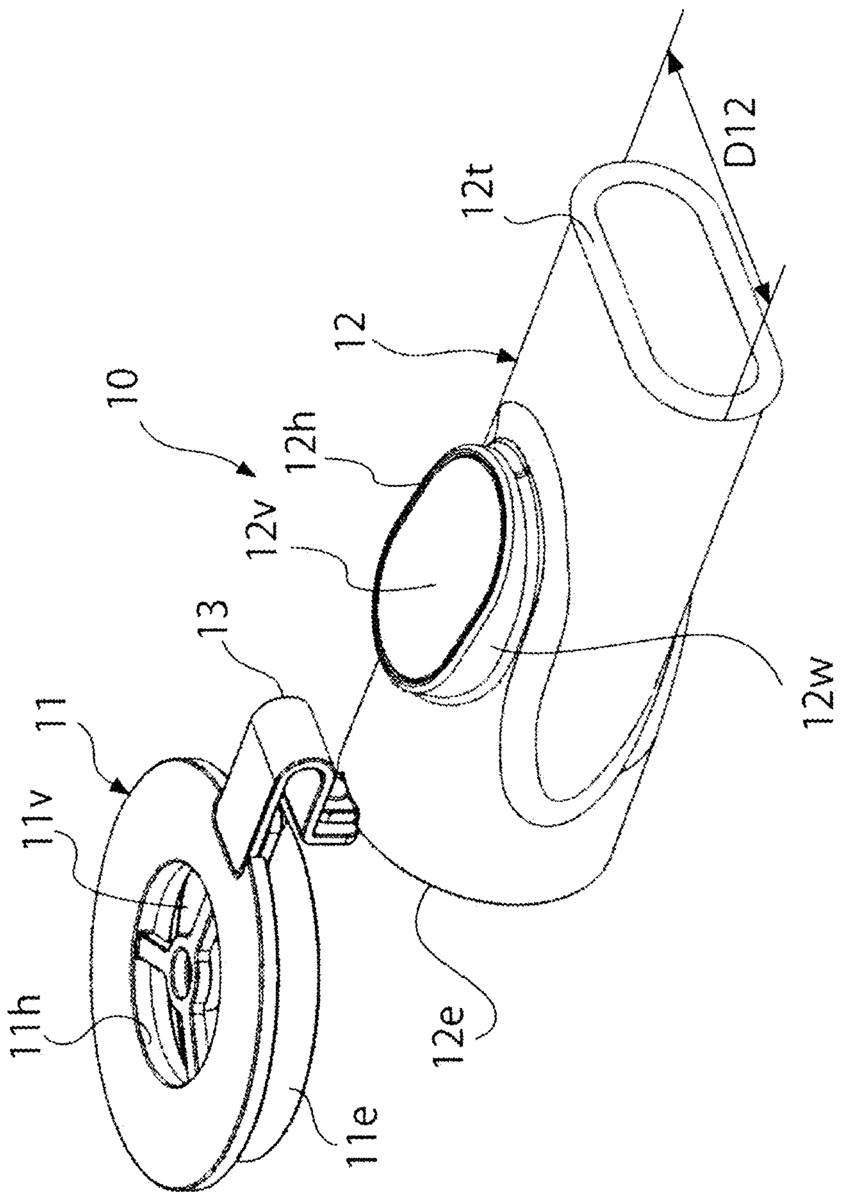
FIG. 9 is an enlarged perspective view of the mouthpiece as viewed from a suction port end portion side.

FIG. 9 is an enlarged perspective view of the mouthpiece 10 shown in FIG. 4 as viewed from the suction port end portion 12$t$ side.

As shown in FIG. 9, the suction port end portion 12$t$ of the second attachment portion 12 of the mouthpiece 10 has a horizontally long flat shape so as to be easily caught by the mouth. A lateral width D12 of the suction port end portion 12$t$ of the mouthpiece 10 is larger than the inner diameter D13 of the attachment end portion 12$e$ of the mouthpiece 10. That is, the lateral width D12 of the suction port end portion 12$t$ of the mouthpiece 10 is larger than the inner diameter D13 of the attachment hole 30$t$ of the inhalation attachment 30. Thus, in a state in which the second attachment portion 12 of the mouthpiece 10 is fitted to the side surface protruding wall portion 22$w$, the inhalation attachment 30 cannot be attached to the second attachment portion 12.

Hereinafter, the use state of the inhalation attachment 30 will be described.

As shown in FIG. 7, the inhalation attachment 30 is used by being attached to the side surface protruding wall portion 22$w$ of the housing body 20 from which the mouthpiece 10 is removed. In the state shown in FIG. 7, the user holds the body portion 20$g$ of the housing body 20 with his/her hand, and performs the inhalation operation and the exhalation operation with the corresponding edge portion 30$e$ fitted to the face.

During the inhalation operation, the outside air is taken into the housing body 20 from the first opening portion 21. The outside air passes through the outside air introduction pipe 24 and is added to the drug solution that has been atomized into atomized particles in the atomization portion 25, thereby generating aerosol. The generated aerosol reaches the second opening portion 22 through the outside of the outside air introduction pipe 24, and is sucked into the human body from the second opening portion 22 through the inhalation attachment 30.

During the exhalation operation, a part of the exhaled air is discharged from the side openings 30$h$ of the inhalation attachment 30, and a part of the exhaled air flowing into the housing body 20 is discharged from the first opening portion 21 to the outside.

Effects of Embodiment

According to the nebulizer kit 8, in a state in which the mouthpiece 10 in which the first attachment portion 11 including the first check valve 11$v$ capable of closing the first opening portion 21 and the second attachment portion 12 including the second check valve 12$v$ are integrally configured is removed from the housing body 20, the first opening portion 21 is always in an open state, and the inhalation attachment 30 different from the mouthpiece 10 becomes able to be attached to the second opening portion 22. Therefore, when the inhalation attachment 30 is used, the first opening portion 21 is in the open state, and even a person having a weak suction force may take the outside air into the housing body 20 in a prepared manner, and may sufficiently inhale the drug solution during the inhalation operation. When a person having a strong suction force uses the mouthpiece 10, the first check valve 11$v$ is always attached to the first opening portion 21. Therefore, the drug solution may be efficiently inhaled.

According to the nebulizer kit 8, the first attachment portion 11 of the mouthpiece 10 attached to the first opening portion 21 of the housing body 20 and the second attachment portion 12 of the mouthpiece 10 attached to the second opening portion 22 of the housing body 20 are integrally configured. Therefore, for example, compared to a structure in which the first attachment portion 11 and the second attachment portion 12 are separated from each other, loss of components may be prevented. In addition, compared to the structure, when the mouthpiece 10 is used, it is possible to prevent the first check valve 11$v$ from being forgotten to be attached, and it is possible to efficiently inhale the drug solution. In addition, compared to this structure, it is possible to prevent the inhalation attachment 30 from performing the inhalation in a state in which the first opening portion 21 is closed.

In the nebulizer kit 8, the first opening portion 21 and the first attachment portion 11 are provided with a positioning mechanism that positions the first attachment portion 11 with respect to the first opening portion 21. Therefore, an attachment position of the first attachment portion 11 may be accurately set. In addition, the second attachment portion 12 integrated with the first attachment portion 11 may be accurately attached, and mountability of the mouthpiece 10 may be improved.

In the nebulizer kit 8, since the connecting portion 13 of the mouthpiece 10 is configured to be elastically deformable, the mouthpiece 10 may be easily attached and detached.

The nebulizer kit 8 is configured such that the inhalation attachment 30 cannot be attached to the second attachment portion 12 of the mouthpiece 10. In other words, the outer diameter of the suction port end portion 12$t$ of the mouthpiece 10 is larger than the inner diameter of the attachment hole 30$t$ of the inhalation attachment 30. Therefore, the inhalation attachment 30 cannot be fitted into the suction port end portion 12$t$ of the mouthpiece 10. Accordingly, it is possible to prevent the inhalation attachment 30 from being used while the mouthpiece 10 is attached to the housing body 20.

In the nebulizer kit 8, the first attachment portion 11 of the mouthpiece 10 is attached to the end surface of the housing body 20 in the longitudinal direction, and the second attachment portion 12 of the mouthpiece 10 is attached to the end surface (side surface) of the housing body 20 in the transverse direction. For example, it is assumed that the first opening portion 21 is provided adjacent to the side surface protruding wall portion 22$w$ on the side surface of the housing body 20. In this case, the mouthpiece 10 has a configuration in which the first attachment portion 11 is rotated 90 degrees to the right in FIG. 5. Compared to the configuration of the mouthpiece assumed as such, according to the configuration of the nebulizer kit 8, a thickness (the length in an upper-lower direction in FIG. 5) of the mouthpiece 10 may be reduced, and the mouthpiece 10 may be formed in an elongated shape as a whole. Therefore, the mouthpiece 10 may be easily housed when the mouthpiece 10 is not used, and usability may be improved.

In the nebulizer kit 8, the first opening portion 21 is configured to be larger than the second opening portion 22. Therefore, the drug solution is easily sucked in the inhalation operation when the inhalation attachment 30 is used. Accordingly, even a person having a weak suction force may inhale a sufficient amount of drug solution. The housing body 20 is formed in an elongated cylindrical shape, and the atomization portion 25 is disposed on a side opposite to the first opening portion 21 side. Therefore, even when the inhalation operation is not performed when the inhalation attachment 30 is used, it is possible to prevent the drug solution atomized in the atomization portion from escaping to the outside from the first opening portion 21 as much as possible. The inhalation attachment 30 is provided with the side openings 30*h*. For this reason, it is possible to reduce the amount of fluid flowing from the second opening portion 22 to the inside of the housing body 20 in the exhalation operation when using the inhalation attachment 30, and it is possible to prevent the drug solution atomized in the atomization portion 25 from escaping to the outside from the first opening portion 21 as much as possible.

Also, in the nebulizer kit 8, the fulcrum of the movable portion of the second check valve 12*v* is provided eccentrically toward the suction port end portion 12*t*. For this reason, the second check valve 12*v* that is opened by an air pressure during the exhalation is opened such that the free end portion 12*ve* on a downstream side of the air flow is warped. As a result, the air flow due to the exhalation may be made into a smooth streamline, and the exhaled air may be efficiently discharged in the exhalation operation when using the mouthpiece 10.

Although the embodiment of the present invention has been described above, a shape and structure thereof are not limited to those shown in the drawings, and can be appropriately changed within the scope of the present invention. For example, in a concave and convex fitting shape of the positioning mechanism in the above embodiment, a convex portion and a concave portion may have a reverse configuration. In addition, in the mouthpiece 10, the first attachment portion 11, the second attachment portion 12, and the connecting portion 13 are integrally configured by fixing the three members of the first attachment portion 11, the second attachment portion 12, and the connecting portion 13, but the mouthpiece 10 may be configured by integrally molding the first attachment portion 11, the second attachment portion 12, and the connecting portion 13 as a single member. The liquid atomized by the nebulizer 1 is not limited to the drug solution, and may be tap water or the like. The insulation attachment 30 has a mask shape, but may have, for example, a substantially cylindrical mouthpiece shape different from the mouthpiece 10.

Although various embodiments have been described above with reference to the drawings, the present invention is not limited to these examples. It is apparent to those skilled in the art that various changes or modifications can be conceived within the scope described in claims, and it is understood that the changes or modifications naturally fall within the technical scope of the present invention. In addition, the components described in the above embodiment may be freely combined without departing from the spirit of the invention.

What is claimed is:

1. A nebulizer kit comprising:

a housing body that houses an atomizer configured to atomize a liquid, the housing body including a first opening and a second opening;

a mouthpiece integrally including a first attachment and a tubular second attachment, the first attachment including a first check valve, the first attachment being configured to be attachable to and detachable from the first opening, the tubular second attachment including a second check valve, the tubular second attachment configured to be attachable to and detachable from the second opening, and an entirety of the first attachment is movable relative to an entirety of the second attachment; and an inhalation attachment different from the mouthpiece attachable to the second opening in a state in which the mouthpiece is removed from the housing body; wherein when the mouthpiece is used, the first attachment of the mouthpiece is directly attached to the first opening while the tubular second attachment of the mouthpiece is directly attached to the second opening.

2. The nebulizer kit according to claim 1, wherein, in a state in which the mouthpiece is attached to the housing body, the first check valve takes outside air into the housing body in accordance with an inhalation operation using the mouthpiece, and the second check valve delivers exhaled air to outside of the tubular second attachment in accordance with an exhalation operation using the mouthpiece.

3. The nebulizer kit according to claim 1, wherein the first opening and the first attachment are provided with a positioner to position the first attachment with respect to the first opening.

4. The nebulizer kit according to claim 1, wherein the mouthpiece includes a connector that connects the first attachment and the tubular second attachment, and the connector is elastically deformable.

5. The nebulizer kit according to claim 1, wherein the mouthpiece is configured such that the inhalation attachment is not attachable to the tubular second attachment.

6. The nebulizer kit according to claim 1, wherein an outer diameter of at least a part of a suction port end of the mouthpiece is larger than an inner diameter of an attachment of the inhalation attachment to the housing body.

7. The nebulizer kit according to claim 1, wherein the first opening is open in a longitudinal direction of the housing body, and the second opening is open in a transverse direction of the housing body.

8. The nebulizer kit according to claim 1, wherein the first opening is larger than the second opening.

9. The nebulizer kit according to claim 1, wherein a fulcrum of a movable portion of the second check valve is provided eccentrically to a suction port end of the mouthpiece.

10. A nebulizer comprising:

the nebulizer kit according to claim 1;

a main body configured to control the atomizer; and the inhalation attachment.

* * * * *